United States Patent [19]

Sergienko et al.

[11] Patent Number: 4,734,096

[45] Date of Patent: Mar. 29, 1988

[54] INTRAOCULAR PROSTHETIC LENS

[75] Inventors: Nikolai M. Sergienko; Zoya F. Veselovskaya, both of Kiev, U.S.S.R.

[73] Assignee: Gosudarstvenny Institut Usovershenstvovania Vrachei, Kiev, U.S.S.R.

[21] Appl. No.: 11,313

[22] Filed: Feb. 5, 1987

[51] Int. Cl.⁴ .............................................. A61F 2/16
[52] U.S. Cl. ................................................ 623/6
[58] Field of Search .............................................. 623/6

[56] References Cited

U.S. PATENT DOCUMENTS

| | | | |
|---|---|---|---|
| 3,866,249 | 2/1975 | Flom | 623/6 |
| 3,906,551 | 9/1975 | Otter | 623/6 |
| 4,242,760 | 1/1981 | Rainin | 623/6 |
| 4,579,557 | 4/1986 | Federov et al. | 623/6 |
| 4,642,115 | 2/1987 | Sergienko | 623/6 |

FOREIGN PATENT DOCUMENTS

| | | | |
|---|---|---|---|
| WO86/01096 | 2/1986 | PCT Int'l Appl. | 623/6 |
| 1116572A | 5/1985 | U.S.S.R. | 623/6 |

Primary Examiner—Ronald L. Frinks
Attorney, Agent, or Firm—Fleit, Jacobson, Cohn & Price

[57] ABSTRACT

The intraocular prosthetic lens comprises an optic lens, a supporting element shaped as a loop, and another supporting element made up of two rods, each having a first bend past which the rods are facing towards the lens posterior surface and are parallel to each other and a second bend past which the ends of the rods are directed in the opposite sides.

1 Claim, 4 Drawing Figures

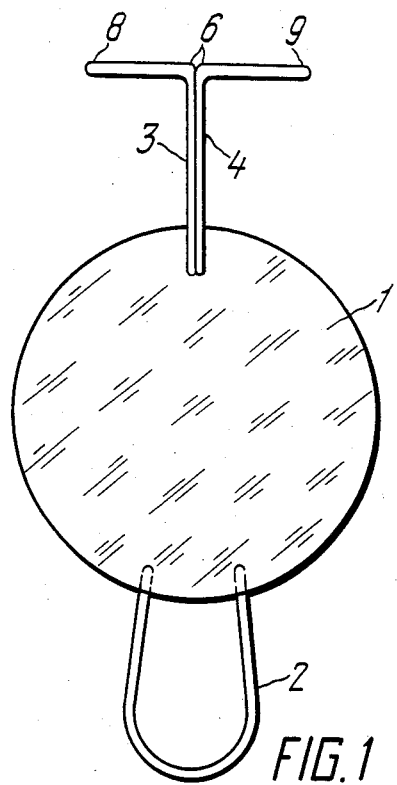
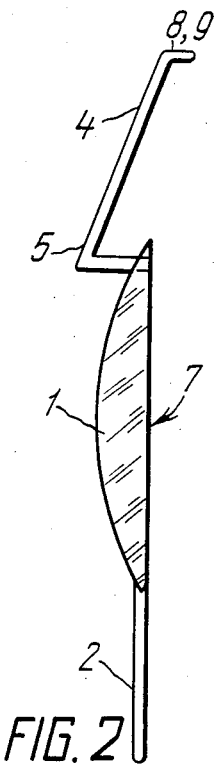

INTRAOCULAR PROSTHETIC LENS

FIELD OF THE INVENTION

The invention relates generally to medical prosthetic devices and more specifically to intraocular prosthetic lenses.

The invention can find application for implanting an intraocular lens in an eye to substitute for the extracted crystalline lens.

BACKGROUND ART

Known in the present state of the art is an intraocular prosthetic lens intended for implantation in the posterior eye chamber, comprising an optical element (lens) and four pairs of supporting elements, which are fixed in position along the perimeter of the lens and are curved arcwise towards the anterior lens surface (cf. U.S. Pat. No. 3,866,249, 1975).

Disadvantages of the aforesaid intraocular prosthetic lens are as follows: too complicated technique of its implantation in the posterior eye chamber through the pupillary orifice due to large size of the prosthetic lens; high degree of traumatism of the implanting procedure due to a necessity of holding the four pairs of supporting elements to the iris by perforating the latter.

Another prior-art intraocular prosthetic lens is known, implantable in the anterior eye chamber and consisting of an optical element (lens) and a number of supporting elements, one of which is loop-shaped, is fixed at the centre of the lens on its posterior surface and has a bend after which the loop is arranged parallel to the lens principal plane. The other supporting element is shaped as a hook is held to the anterior lens surface at the same edge thereof where the first loop-shaped supporting element is situated. The intraocular prosthetic lens is fixed in position by passing the other supporting element through an opening in the iris and bringing it under the former loop-shaped supporting element (cf. U.S. Pat. No. 3,906,551, 1975).

A disadvantage of the aforesaid intraocular prosthetic lens resides in a complicated technique of its holding involving high degree of traumatism.

One more intraocular prosthetic lens is known in the present state of the art, comprising an optic lens and a number of supporting elements, one of which is shaped as a loop, while the other is composed of two rods, each having two bends. The first bend is spaced from the lens anterior surface a distance which is 1.5 times the lens thickness, and the rods diverge, after the first bend, towards the lens posterior surface. The second bend is coplanar with the lens and the rod ends are directed towards each other (cf. USSR Inventor's Certificate No. 1116572, Int.Cl. A61F 1/16, 1985). A disadvantage inherent in the aforesaid invention resides in that its fixing to the iris requires holes in the latter which inflicts injury upon the iris.

SUMMARY OF THE INVENTION

The invention has for its object to provide an intraocular prosthetic lens which would not inflict injury upon the ocular tissues when being implanted therein.

Said object is accomplished due to the fact that in an intraocular prosthetic lens, comprising an optic lens, a first supporting element curved into a loop, and a second supporting element diametrically opposite to the first and made up of two rods, each having a first bend so made that the rods are facing towards the posterior lens surface, and a second bend coplanar with the lens principal plane, according to the invention, the rods of the second supporting elements are parallel past the first bend, while past the second bend their ends are facing towards the opposite sides.

SUMMARY OF THE DRAWINGS

The foregoing and other objects and advantages of the present invention will become more apparent from a consideration of a detailed description of some specific embodiments thereof with reference to the accompanying drawings, wherein:

FIG. 1 is a front view of the intraocular prosthetic lens, according to the invention;

FIG. 2 is a side view of FIG. 1;

DETAILED DESCRIPTION OF THE INVENTION

Figure 3:
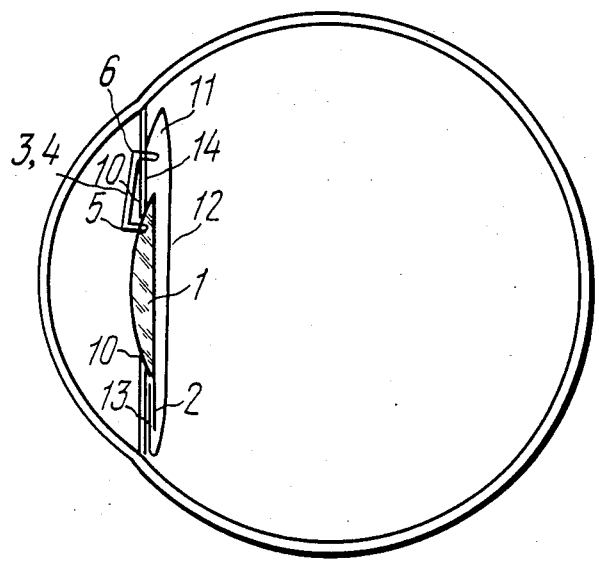
FIG. 3 is a side view of the intraocular prosthetic lens when implanted in the eye, according to the invention.

The intraocular prosthetic lens comprises an optic lens 1 (FIGS. 1,2) and two supporting elements made fast diametrically opposite on the lens 1. The first supporting element is shaped as a loop 2, The second supporting element comprises two rods 3, 4 both featuring a vacant or free end and each of which has two bends 5, 6. Past the first bend 5 the rods 3 and 4 are facing towards a posterior surface 7 (FIG. 2) of the lens 1 and are parallel to each other as shown in FIG. 1. The second bend 6 is coplanar with the principal plane of the lens 1, while past the second bend 6 vacant or free ends 8, 9 of the respective rods 3, 4 are directed oppositely to each other.

It has been found that the first bend is most expedient to be spaced 0.7 mm apart from the surface of the lens 1, when the rods 3, 4 are held to that portion of the lens 1 which is 0.4 mm thick.

The implantation technique of the proposed intraocular prosthetic lens is as follows.

Figure 4:
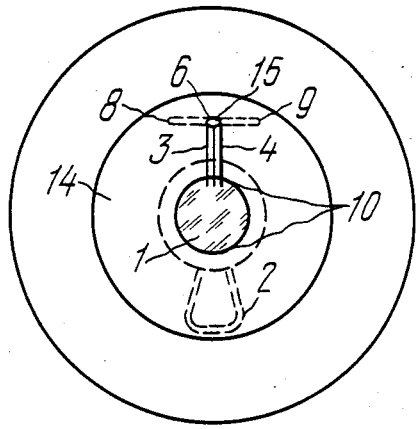
FIG. 4 is a front view of FIG. 3.

Once the cataract has been extracted extracapsularly, that is, with the posterior lenticular capsule remaining intact, the intraocular prosthetic lens is brought into a posterior eye chamber 11 via a pupillary orifice 10 (FIGS. 3, 4). In this case the loop 2 is situated between a posterior lenticular capsule 12 and the residual portion of an anterior lentiocular capsule 13, while the rods 3,4 are located in front of an iris 14. The first bend 5 of the rods 3, 4 is at the edge of the pupillary orifice 10, while the second bend 6 lies in the plane of the iris 14.

Then the rods 3, 4 are brought, past the second bend thereof, into a preliminarily made opening 15 located in the region of the root of the iris 14, so that the ends 8, 9 of the rods 3, 4 should be in the posterior eye chamber 11.

Implantation of the proposed intraocular prosthetic lens has been performed on 18 eyes under clinical conditions. All the patients operated upon have visual acuity within 0.5 and 1.0.

A female patient aged 56 with the diagnosis of mature cataract on the right eye (visual acuity -correct light projection) was subjected to extracapsular cataract extraction followed by implantation of the proposed intraocular prosthetic lens. Postoperative coursing smooth and uneventful. On dismissal from the clinic the visual acuity of the eye operated upon is 0.7.

A female patient aged 64 with the diagnosis of mature cataract on the left eye (visual acuity - correct light projection) was subjected to extracapsular cataract extraction followed by implantation of the proposed intraocular prosthetic lens. On dismissal from the clinic the visual acuity of the eye operated upon is 0.6.

The proposed intraocular prosthetic lens makes it possible to use simple implantation technique which reduces the degree of traumatism inflicted upon the ocular tissues. Unrestricted use may be made in the post-operative period of mydriatics which makes the postoperative period more facile.

What is claimed is:

1. An intraocular prosthetic lens, comprising:
   an optic lens having a principal plane, an anterior surface, and a posterior surface;
   a first supporting element secured on said optic lens and shaped as a loop;
   a second supporting element, secured on said optic lens diametrically opposite with respect to said first supporting element and having a first and a second rod, both featuring a vacant end; said first and said second rods having a first bend spaced somewhat apart from said anterior surface of said optic lens; past said first bend said first and second rods are parallel to each other and are facing towards said posterior surface of said optic lens; said first and said second rods have a second bend coplanar with said principal plane of said optic lens, past which bend said vacant ends of said first and said second rod are directed oppositely to each other.

* * * * *